United States Patent

Yamamoto et al.

[11] 4,048,168
[45] Sept. 13, 1977

[54] PROCESS FOR PREPARING 1-POLYHALOALKYL-3,4-DIHYDRO-2-(1H)-QUINAZOLINONES

[75] Inventors: Michihiro Yamamoto, Nishinomiya; Shigenari Katayama, Takarazuka; Masao Koshiba, Nishinomiya; Hisao Yamamoto, Kobe, all of Japan

[73] Assignee: Sumitomo Chemical Company, Limited, Osaka, Japan

[21] Appl. No.: 754,640

[22] Filed: Dec. 27, 1976

[30] Foreign Application Priority Data

Jan. 23, 1976   Japan .................................. 51-6920

[51] Int. Cl.$^2$ ......................................... C07D 239/82
[52] U.S. Cl. ............................................. 260/251 QB
[58] Field of Search ................................. 260/251 QB

[56] References Cited

U.S. PATENT DOCUMENTS 3,748,331   7/1973   Cooke et al. .................. 260/251 QB

*Primary Examiner*—Raymond V. Rush
*Attorney, Agent, or Firm*—Stevens, Davis, Miller & Mosher

[57] ABSTRACT

3,4-Dihydro-2(1H)-quinazolinone derivatives of the formula,

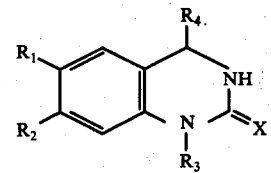

wherein $R_1$ and $R_2$ are each hydrogen, lower alkyl, lower alkylthio or lower alkoxy, or, when taken together, $R_1$ and $R_2$ may form methylenedioxy; $R_3$ is polyhalo-lower alkyl; $R_4$ is phenyl, halophenyl, lower alkoxyphenyl, lower alkylphenyl or thienyl; and X is oxygen or sulfur, which are known to be very useful intermediates for the preparation of anti-inflammatory and analgesic agents, are obtained in a high yield by reacting a compound of the formula,

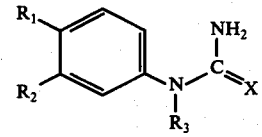

wherein $R_1$, $R_2$, $R_3$ and X are as defined above, with a compound of the formula, $$R_4-CHO$$

wherein $R_4$ is as defined above, with heating in the presence of a zinc halide as a catalyst.

4 Claims, No Drawings

PROCESS FOR PREPARING 1-POLYHALOALKYL-3,4-DIHYDRO-2-(1H)-QUINAZOLINONES

This invention relates to a novel process for the preparation of 3,4-dihydro-2(1H)-quinazolinone derivatives.

More particularly, this invention pertains to a process for producing 3,4-dihydro-2(1H)-quinazolinone derivatives of the formula,

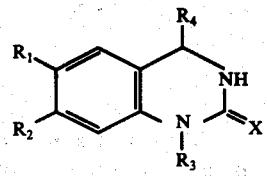

(I)

wherein $R_1$ and $R_2$ are each independently hydrogen, lower alkyl, lower alkylthio or lower alkoxy, or, when taken together, $R_1$ and $R_2$ may form methylenedioxy; $R_3$ is polyhalo-lower alkyl; $R_4$ is phenyl, halophenyl, lower alkoxyphenyl, lower alkylphenyl or thienyl; and X is oxygen or sulfur, which comprises reacting a compound of the formula,

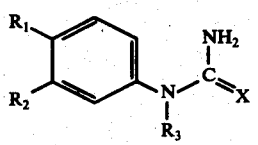

(II)

wherein $R_1$, $R_2$, $R_3$ and X are as defined above, with a compound of the formula,

$R_4$—CHO  (III)

wherein $R_4$ is as defined above, with heating in the presence of a zinc halide.

As used herein, the term "lower alkyl" means alkyl having 1 to 4 carbon atoms (e.g. methyl, ethyl, n-propyl, isopropyl, n-butyl or isobutyl); "lower alkoxy" means alkoxy having 1 to 4 carbon atoms (e.g. methoxy, ethoxy, n-propoxy, isopropoxy, n-butoxy or isobutoxy); "lower alkylthio" means alkylthio having 1 to 4 carbon atoms (e.g. methylthio, ethylthio, n-propylthio, isopropylthio, n-butylthio); "polyhalolower alkyl" means, for example, 2,2-difluoroethyl, 2-chloro-2,2-difluoroethyl, 2,2,2-trifluoroethyl, 2,2,3,3-tetrafluoropropyl, and 2,2,3,3,3-pentafluoropropyl; "halophenyl" may mean o-fluorophenyl, p-fluorophenyl, o-chlorophenyl, m-chlorophenyl or p-chlorophenyl; and "lower alkylphenyl" or "lower alkoxyphenyl" means o-, m-, or p-lower alkyl or lower alkoxy substituted phenyl.

The said 3,4-dihydro-2(1H)-quinazolinone derivatives of the formula (I) have been already known to have anti-inflammatory and analgesic activities, and to be very useful intermediates for the preparation of anti-inflammatory and analgesic agents of the formula,

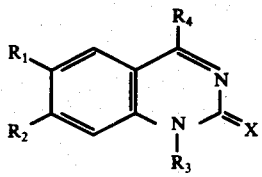

(IV)

wherein $R_1$, $R_2$, $R_3$, $R_4$ and X are as defined above. Namely the compounds of the above formula (IV) can be easily prepared by oxidation of the compounds of the formula (I) according to known processes.

Hitherto, there have been disclosed a process for producing the compounds of the formula (I) in U.S. Pat. Nos. 3,748,331 and 3,829,420, wherein the compounds of the formula (II) are reacted with the compounds of the formula (III). These Patents also disclose that the use of arylsulfonic acids, alkylsulfonic acids, trifluoroacetic acid or hydrogen chloride as a catalyst is suitable. According to the prior process, however, even in case methanesulfonic acid, which is described as a preferred one among these known catalysts, is used, the yield of the objective compounds the formula (I) is about 20% at best, and moreover a large quantity of by-products are formed, when the compounds of the formula (II) wherein X is oxygen are used as a starting material. Furthermore, when the compounds of the formula (II) wherein X is sulfur are used as a starting material, the objective compounds of the formula (I) can hardly be obtained by the known method.

In order to solve such problems of the known process, the inventors have extensively studied the conditions of this reaction and found that, when the reaction is carried out by using a zinc halide as catalyst, the desired 3,4-dihydro-2(1H)-quinazolinone derivatives are obtained in remarkable good yield with high purity.

In carrying out the process of the present invention, the amount of zinc halide used, is preferably in the range of 1 to 5 molar equivalents based on the compound of the formula (II). A suitable zinc halide may be zinc chloride or zinc bromide.

The present process may be carried out either in the presence or absence of an inert solvent. However, it is preferable to carry out the reaction by heating under reflux in an inert solvent such as toluene, xylene, chlorobenzene, o-chlorotoluene, tetrachloroethane or the like, while removing the water formed azeotropically using a water separator.

The following examples are given to illustrate the present invention more precisely, but they should not be interpreted to restrict the present invention thereto.

EXAMPLE 1

A mixture of 3.23 g (0.013 mole) of N-(2,2,2-trifluoroethyl)-N-(p-methoxyphenyl)urea, 1.6 g (0.015 mole) of benzaldehyde, 5.3 g (0.039 mole) of anhydrous zinc chloride, and 65 ml of xylene was stirred for a while and then heated under reflux for 15 hours, removing the water formed azeotropically. Thereafter, 20 ml of 1N-hydrochloric acid was added to the reaction mixture and the mixture was stirred for a while. The organic layer was separated from the reaction mixture, washed with water, dried over anhydrous sodium sulfate, and evaporated under reduced pressure. The resulting residue was treated with isopropyl alcohol to give 2.71 g (62%) of 1-(2,2,2-trifluoroethyl)-4-phenyl-6-methoxy-3,4-dihydro-2(1H)-quinazolinone, m.p. 168°–169° C.

EXAMPLE 2

According to substantially the same procedures as that of Example 1, the following compounds were obtained from the corresponding starting compounds (II) and the compounds (III).

1-(2,2-Difluoroethyl)-4-phenyl-6-methoxy-3,4-dihydro-2(1H)-quinazolinone, m.p. 128°–129° C;

1-(2-Chloro-2,2-difluoroethyl)-4-phenyl-6-methoxy-3,4-dihydro-2(1H)-quinzolinone, m.p. 158°–159° C;

1-(2,2,2-Trifluoroethyl)-4-phenyl-6,7-methylenedioxy-3,4-dihydro-2(1H)-quinazolinone, m.p. 199°–200° C;

1-(2,2,3,3-Tetrafluoropropyl)-4-phenyl-6-methoxy-3,4-dihydro-2(1H)-quinazolinone, m.p. 138°–139° C;

1-(2,2,3,3,3-Pentafluoropropyl)-4-phenyl-6-methoxy-3,4-dihydro-2(1H)-quinazolinone, m.p. 135°–136° C;

1-(2,2,3,3,3-Pentafluoropropyl)-4-phenyl-6-methyl-3,4-dihydro-2(1H)-quinazolinone, m.p. 155°–156° C;

1-(2,2,2-Trifluoroethyl)-4-(2-thienyl)-6-methoxy-3,4-dihydro-2(1H)-quinazolinone, m.p. 178°–179° C;

1-(2,2,2-Trifluoroethyl)-4-phenyl-6-methoxy-3,4-dihydro-2(1H)-quinazolinethione, m.p. 199°–199.5° C.

What is claimed is:

1. A process for preparing a 3,4-dihydro-2(1H)-quinazolinone derivative of the formula,

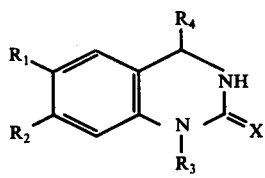
(I)

wherein $R_1$ and $R_2$ are each independently hydrogen, lower alkyl, lower alkylthio or lower alkoxy, or, when taken together, $R_1$ and $R_2$ may form methylenedioxy; $R_3$ is polyhalo-lower alkyl; $R_4$ is phenyl, halophenyl, lower alkoxyphenyl, lower alkylphenyl or thienyl; and X is oxygen or sulfur, which comprises reacting a compound of the formula,

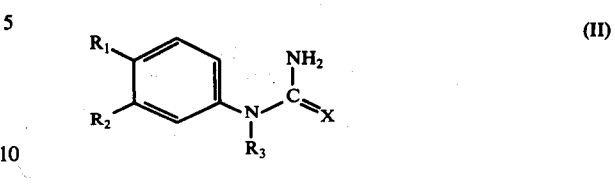
(II)

wherein $R_1$, $R_2$, $R_3$ and X are as defined above, with a compound of the formula, $R_4$—CHO     (III)

wherein $R_4$ is as defined above, with heating in the presence of a zinc halide, optionally in an inert solvent.

2. A process according to claim 1, wherein the zinc halide is used in an amount of 1 to 5 molar equivalents based on the compound (II).

3. A process according to claim 1, wherein the zinc halide is zinc chloride or zinc bromide.

4. A process according to claim 1, wherein the reaction is carried out by heating under reflux in an inert solvent selected from the group consisting of toluene, xylene, chlorobenzene, o-chlorotoluene and tetrachloroethane, while removing the water formed azeotropically.

* * * * *